United States Patent [19]

Chapman et al.

[11] Patent Number: 5,792,455
[45] Date of Patent: Aug. 11, 1998

[54] ANTI-IDIOTYPIC ANTIBODY VACCINES

[75] Inventors: Paul B. Chapman; Alan N. Houghton, both of New York, N.Y.

[73] Assignee: Sloan-Kettering Institute for Cancer Research, New York, N.Y.

[21] Appl. No.: 619,217

[22] Filed: Mar. 21, 1996

[51] Int. Cl.$^6$ .................... A61K 45/05; A01H 63/00; C07K 16/00
[52] U.S. Cl. .................... 424/131.1; 424/282.1; 424/93.46; 530/387.2
[58] Field of Search .................... 424/131.1, 282.1, 424/93.46; 530/387.2

[56] References Cited

U.S. PATENT DOCUMENTS 5,529,922  6/1996  Chapman et al. .................... 435/240.27

OTHER PUBLICATIONS

Forstrom, et al., "Immunization To A Syngeneic Sarcoma By A Monoclonal Auto-anti-idiotypic Antibody", Nature, Jun. 1983, Nature, vol. 303, pp. 627–629 (Exhibit 17).
Hastings, et al., "Production And Characterization Of A Murine/Human Chimeric Anti-idiotype Antibody That Mimics Ganglioside", Cancer Research, Apr. 1992, vol. 52, pp. 1681–1686 (Exhibit 18).
Hellstrom, "Strong Antitumor Activities Of IgG3 Antibodies To A Human Melanoma-associated Ganglioside", PNAS, Mar. 1985, vol. 82, pp. 1499–1502 (Exhibit 19).
Hird, et al., "Immunotherapy With Monoclonal Antibodies", Genes and Cancer, 1990, pp. 183–189 (Exhibit 20).
Hodgson, "Making Monoclonals In Microbes", Biotechnology 1991, vol. 9, pp. 421–424 (Exhibit 21).
Houghton, et al., "Mouse Monoclonal IgG3 Antibody Detecting $G_{D3}$Ganglioside: A Phase I Trial In Patients With Malignant Melanoma", PNAS 1985, vol. 82, pp. 1242–1246 (Exhibit 22).
Kerlin, et al., "Variations In Immunoglobulin Isotype Produced During the Antibody Response To *Brucella Abortus* and *Staphylococcus Aureus* Vaccines In Sheep", Research in Veterinary Science, 1986, vol. 41, pp. 191–195 (Exhibit 23).
Koprowski, et al., "Human Anti-idiotype Antibodies In Cancer Patients: Is The Modulation Of The Immune Response Beneficial For The Patient?", PNAS, Jan. 1984, vol. 81, pp. 216–219 (Exhibit 24).
Livingston, et al., "Serological Response Of Melanoma Patients To Vaccines Prepared From VSV Lysates Of Autologous And Allogenic Cultured Melanoma Cells", Cancer 1985, vol. 55, pp. 713–720 (Exhibit 25).
Miller, et al., "Shared Idiotypes Expressed By Human B–Cell Lymphomas", New England Journal of Medicine, 1989, vol. 321, No. 13, pp. 851–857 (Exhibit 26).
Morrison, et al., "Transfectomas Provide Novel Chimeric Antibodies", Science 1985, vol. 229, pp. 1202–1207 (Exhibit 27).
Morrison, et al., "Production And Characterization Of Genetically Engineered Antibody Molecules", Clinical Chemistry, 1988, vol. 34, pp. 1668–1675 (Exhibit 28).

Nepom, et al., "Anti-idiotypic Antibodies And The Induction Of Specific Tumor Immunity", Cancer and Metastasis Reviews, 1987, vol. 6, pp. 489–502 (Exhibit 29).
Nepom, et al., "Induction Of Immunity To A Human Tumor Marker By In Vivo Administration Of Anti-idiotypic Antibodies In Mice", PNAS, vol. 81, May 1984, pp. 2864–2867 (Exhibit 30).
Oi, et al., "Chimeric Antibodies", Biotechniques 1986, vol. 4, pp. 214–221 (Exhibit 31).
Saroj Vadhan-Raj, et al., "Phase I Trial Of A Mouse Monoclonal Antibody Against GD3 Ganglioside In Patients With Melanoma: Induction Of Inflamatory Response At Tumor Sites", Journal of Clinical Oncology 1988, vol. 6, No. 10, pp. 1636–1648 (Exhibit 33).
Schreiber, et al., "Anti-Idiotype Induced, LPS–Specific Antibody Response To Pseudomonas Aeruginosa", Clinical Research, 1988, vol. 36, No. 3 (Exhibit 34).
Shin, "Production And Properties Of Chimeric Antibody Molecules", Methods in Enzymology, 1989, vol. 178, pp. 459–476 (Exhibit 35).
Soederstroem, et al., "The *Escherichia Coli* K1 Capsule Shares Antigenic Determinants With The Human Gangliosides GM3 and GD3", Chemical Abstracts, Jun. 1984, vol. 100, p. 425 (Exhibit 36).
Staruch, et al., "The Adjuvanticity Of Interleukin 1 In Vivo", Journal of Immunology 1983, vol. 130, pp. 2191–2194 (Exhibit 37).
Stein, "Neonatal Administration Of Idiotype Or Antidiotype Primes For Protection Against *Escheria Coli* K13 Infection In Mice", Journal of Experimental Medicine 1984, vol. 160, pp. 1001–1011 (Exhibit 38).
Tadashi, T., et al., "Immunogenicity Of Melanoma-associated Gangliosides In Cancer Patients", In. J. Cancer, 1985, vol. 35, pp. 607–612 (Exhibit 39).
Viale, et al., "Anti-human Tumor Antibodies Induced In Mice And Rabbits By Internal Image Anti-idiotypic Monoclonal Immunoglobulins", J. Immunology, Dec. 15, 1987, vol. 139, pp. 4250–4255 (Exhibit 40).
Viale, et al., "Idiotypic Replica Of An Anti–Human Tumor 15. Associated Antigen Monoclonal Antibody", J. Immunology, Dec. 1989, vol. 143, pp. 4338–4344 (Exhibit 41).
Yeh, et al., "Mouse Monoclonal Anti-Idiotypic Antibody To MG-21, A Mouse IgG3 Monoclonal Antibody To A Human Melanoma–Associated GD3 Ganglioside Antigen", Proceedings of AACR, Mar. 1987, vol. 28, p. 388, Abstract No. 1538 (Exhibit 42).

(List continued on next page.)

*Primary Examiner*—Lila Feisee
*Assistant Examiner*—Geetha P. Bansal
*Attorney, Agent, or Firm*—John P. White; Cooper & Dunham LLP

[57] ABSTRACT

A vaccine for stimulating and enhancing in a subject to which the vaccine is administered, production of antibodies which recognize GD3 ganglioside, comprising an effective amount of anti-idiotypic monoclonal antibody, designated BEC2, an effective amount of the appropriate adjuvant and a pharmaceutically acceptable vehicle.

9 Claims, 6 Drawing Sheets

OTHER PUBLICATIONS

Young, et al., "Production Of Monoclonal Antibodies Specific For Two Distinct Steric Portions Of The Glycolipid Ganglio-N-Triosylceramide", Oct. 1979, Journal of Experimental Medicine, vol. 150, pp. 1008–1019 (Exhibit 43).

Waldmann, T., "Monoclonal Antibodies In Diagnosis And Therapy", Science, Jun. 1991, vol. 252, pp. 1657–1662 (Exhibit 44).

Wei, et al., "Improved Anti-tumor Reactivity With Monoclonal Anti-idiotypic Antibody Conjugated To Syngeneic Mouse Red Blood Cells", J. Immunology Methods, 1989, vol. 122, pp. 227–234 (Exhibit 45).

Cheresh, et al., "Disialoganglioside GD3 On Human Melanoma Serves As A Relevant Target Antigen For Monoclonal Antibody-mediated Tumor Cytolysis" PNAS 1985, vol. 82, pp. 5155–5159 (Exhibit 14).

Davis, et al., "Antibody and HIV-1 gp120 Recognition Of CD4 Undermines The Concept of Mimicry Between Antibodies And Receptors", Nature 1992, vol. 358, pp. 76–79 (Exhibit 15).

Dippold, et al., "Cell Surface Antigens Of Human Malignant Melanoma: Definition Of Six Antigenic Systems With Mouse Monoclonal Antibodies", PNAS, 1980, vol. 77:10, pp. 6114–6118 (Exhibit 16).

BEC2/BCG: Overall Survival all patients (14 Pts. 10 Censored)
Tick Mark (l) indicates last follow-up

ANTI-IDIOTYPIC ANTIBODY VACCINES

The invention disclosed herein was made with the support of the NCI Grant No. PO1-CA33049. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

GD3 ganglioside is an appealing target for immunotherapy of melanoma for several reasons. Expression of the GD3 ganglioside on normal tissue is selective and occurs at low concentrations. Expression of the GD3 ganglioside is abundant on most melanoma (Hamilton et al., 1993) and antibodies to GD3 can both block melanoma cell attachment to surfaces (Cheresh, et al., 1986; Chapman, et al., 1990), an early critical step in invasion and metastasis, and can inhibit melanoma cell growth in vitro (Dippold, et al., 1984). In animal models, monoclonal antibodies (MAb) R24 against GD3 can inhibit outgrowth of melanoma tumors and treatment of metastasic melanoma patients with the anti-GD3 MAb R24 can result in major tumor shrinkage (Vadhan-Raj, et al., 1988; Caufield, et al., 1990; Raymond, et al., 1991; Creekmore, et al., 1992). However, GD3 is poorly immunogenic, and attempts to immunize patients against GD3 using GD3$^+$ cells, purified GD3, or GD3 conjugates have been unsuccessful (Tai, et al., 1985; Livingston, et al., 1989).

The U.S. application No. 08/445,906, filed May 19, 1995, which is continuation of U.S application No. 08/111,262, filed Aug. 24, 1993, which is a continuation of U.S. Ser. No. 07/357,037, filed May 25, 1989, has been issued. This application discloses an anti-idiotypic monoclonal antibody, BEC2 made against the anti-GD3 monoclonal antibody R24 and a method to produce the same. The anti-idiotypic monoclonal antibody, BEC2 carries the internal image of GD3 and then mimics GD3. Such monoclonal antibody is a valuable immunological reagent. Patients were immunized with BEC2 administered subcutaneously without an immune adjuvant; only 55% of patients developed anti-BEC2 antibodies and only 1/20 developed detectable anti-GD3 antibodies.

Potent immunological adjuvants, as QS21 and BCG, have been used to enhance the immune response to ganglioside and to anti-idiotypic MAb (Mittelman, et al., 1992). QS21 is a saponin extracted from the bark of the South American soap bark tree *Quillaja saponaria* Molina with significant adjuvant activity (Kensil, et al., 1991; Wu, et al., 1992; Newman, et al., 1992; White, et al., 1991). Because of its wide spread use, high adjuvant effect and low toxicity QS21 is best selected. BCG is an attenuated strain of *Mycobacterium bovis* and is a potent immunological adjuvant that has been used to enhance the immune response to gangliosides (Livingston, et al., 1994) and to anti-idiotypic MAb (Mittelman, et al., 1992).

SUMMARY OF THE INVENTION

The present invention provides a vaccine comprising an effective amount of the anti-idiotypic monoclonal antibody designated BEC2, an effective amount of the appropriate adjuvant and a pharmaceutically acceptable vehicle that enhance the production of antibodies against GD3.

The present invention also provides a method for enhancing and stimulating production of antibodies against GD3 in a melanoma subject which comprises administering to the subject a vaccine comprising an effective amount of the anti-idiotypic monoclonal antibody designated BEC2, an effective amount of the appropriate adjuvant and a pharmaceutically acceptable vehicle.

The present invention further provides a method for treating melanomas patients which comprises administering to the subject a vaccine comprising an effective amount of the anti-idiotypic monoclonal antibody designated BEC2, an effective amount of the appropriate adjuvant and a pharmaceutically acceptable vehicle.

The present invention further provides a method for preventing recurrence of melanomas which comprises administering to the subject a vaccine comprising an effective amount of the anti-idiotypic monoclonal antibody designated BEC2, an effective amount of the appropriate adjuvant and a pharmaceutically acceptable vehicle.

In one embodiment of the invention, the invention provides a method for increasing the survival rate of small cell lung cancer patients which comprises administering to the subject a vaccine comprising an effective amount of the anti-idiotypic monoclonal antibody designated BEC2, an effective amount of the appropriate adjuvant and a pharmaceutically acceptable vehicle.

BRIEF DESCRIPTION OF THE FIGURES

FIG. 1:

A. Reactivity of immune serum from patient 13 immunized with BEC2/BCG against BEC2 (●) and MPC11 (■). After 5 immunizations immune serum is diluted as shown and tested for binding to BEC2 and MPC11 as described in the Experimental section.

B. Mean reactivity of immune sera against BEC2 (solid bars) or MPC11 (open bars) in patients immunized with BEC2/BCG (N=14) or BEC2/QS21 (N=6). Each serum sample is tested at a dilution that resulted in absorbance readings of approximately 0.5 against BEC2-coated plates. Error bars represent standard deviation of the mean.

C. Binding of pre-absorbed serum from patient 13 immunized with BEC2/BCG against BEC2 (●) and MPC11 (■). The same serum as shown in FIG. 1A (diluted to 1:100,000) is exhaustively absorbed against MPC11-coated agarose beads prior to performing the assay.

FIG. 2:

A. Anti-GD3 antibody titers induced by BEC2/BCG in patient 1. Serological assays were performed as described in the Experimental section. Arrows indicate immunization with BEC2/BCG. In this patient, anti-GD3 reactivity was detected only with alkaline phosphatase-conjugated second antibody against human IgG.

B. Anti-GD3 antibody titers induced by BEC2/BCG in patient 3. Serological assays were performed as described in the Experimental section. Arrows indicate immunization with BEC2/BCG. In this patient, anti-GD3 reactivity was detected only with alkaline phosphatase-conjugated second antibody against human IgG.

C. Anti-GD3 antibody titers induced by BEC2/BCG in patient 13. Serological assays were performed as described in the Experimental section. Arrows indicate immunization with BEC2/BCG. In this patient, anti-GD3 reactivity was detected only with alkaline phosphatase-conjugated second antibody against human IgG.

DETAILED DESCRIPTION OF THE INVENTION

The present invention provides a vaccine comprising an anti-idiotypic monoclonal antibody designated BEC2, an effective amount of an appropriate adjuvant and a pharmaceutically acceptable vehicle for stimulating or enhancing in a subject to which the vaccine is administered, production of antibodies against GD3 ganglioside.

A hybridoma designated BEC2 hybridoma which produces the anti-idiotypic monoclonal antibody is also provided in the invention. The BEC2 hybridoma was deposited on May 23, 1989 with the American Type Culture Collection (ATCC), 12301 Parklawn Drive, Rockville, Md. 20852, U.S.A. under the provisions of the Budapest Treaty for the International Recognition of the Deposit of Microorganisms for the Purposes Of Patent Procedure. The hybridoma BEC2 was assigned ATCC Accession No. HB 10153.

The present invention also provides a method for enhancing and stimulating production of antibodies against GD3 in a melanoma subject which comprises administering to the subject a vaccine comprising an effective amount of the anti-idiotypic monoclonal antibody designated BEC2, an effective amount of an appropriate adjuvant and a pharmaceutically acceptable vehicle.

The present invention further provides a method for treating melanoma in a subject which comprises administering to the subject a vaccine comprising an effective amount of the anti-idiotypic monoclonal antibody designated BEC2, an effective amount of an appropriate adjuvant and an pharmaceutically acceptable vehicle.

The present invention further provides a method for preventing recurrence of cancer which comprises administering to a melanoma subject a vaccine comprising an effective amount of the anti-idiotypic monoclonal antibody designated BEC2, an effective amount of an appropriate adjuvant and an acceptable pharmaceutical vehicle.

In one embodiment of the invention, the invention provides a method for increasing the survival rate of small cell lung cancer patients which comprises administering to the subject a vaccine comprising an effective amount of the anti-idiotypic monoclonal antibody designated BEC2, an effective amount of the appropriate adjuvant and an pharmaceutically acceptable vehicle.

In another embodiment of the invention, the invention provides a method for increasing the survival rate of small cell lung cancer patients which comprises administering to the subject a vaccine comprising an effective amount of the anti-idiotypic monoclonal antibody designated BEC2, an effective amount of the appropriate adjuvant and an pharmaceutically acceptable vehicle in combination with a treatment with a chemotherapeutic agent.

In another embodiment of the invention, the appropriate adjuvant is BCG.

In another embodiment of the invention, the effective amount of the anti-idiotypic monoclonal antibody, BEC2, ranges from about 0.5 mg to about 25 mg.

In another embodiment of the invention, the effective amount of the anti-idiotypic monoclonal antibody, BEC2, is about 2.5 mg.

Different effective amounts of the anti-idiotypic monoclonal antibody, BEC2 thereof may be used according to this invention. A person ordinary skilled in the art can perform simple titration experiments to determine what effective amount is required for effective immunization. An example of such titration experiment is to inject different amounts of the anti-idiotypic monoclonal antibody, BEC2, from 0.5 mg to 32 mg, to make a seroconversion and then examine the immune response.

In another embodiment of the invention, the adjuvant is BCG and an effective amount of BCG is about $10^7$ Colony Forming Units (CFU).

Different effective amounts of the appropriate adjuvant thereof may be used according to this invention. A person ordinary skilled in the art can perform simple titration experiments to determine what effective amount is required for effective immunization. An example of such titration experiment is to inject different amounts of the appropriate adjuvant and then examine the immune response.

In another embodiment of the invention, the vaccine comprising 2.5 mg of BEC2 and attenuated doses of BCG is injected in weeks 0,2,4,6 and 10.

In another embodiment of the invention, subsequent doses of BCG are 3-fold attenuated.

In another embodiment of the invention, the vaccine is injected intradermally, subcutaneously or intravenously.

A pharmaceutically acceptable carrier includes all carriers known in the art.

The invention will be better understood from the Experimental Details which follow.

EXPERIMENTAL DETAILS:

First Series of Experiments:

Material and Methods

Patients Selection

Sequential clinical trials in which melanoma patients free of disease after complete surgical resection but at high risk for recurrence are immunized with BEC2 mixed with BCG (BEC2/BCG) using 2.5 mg of BEC2. Patients free of disease after resection of AJCC stage II are also eligible if the primary tumor was ≧4 mm deep. Other eligibility requirements are: normal WBC and differential count, no previous chemotherapy, immunotherapy, or radiation therapy within the previous month, and no history of other malignancies within the past 5 years. Patients are excluded if they have significant underlying medical problems (e.g. NYHA class III or IV cardiac disease, active infections requiring antibiotics, or active bleeding), required antihistamines, steroids, or non-steroidal anti-inflammatory drugs, have an immunodeficiency or are asplenic, have a history of metastases to the CNS, or are pregnant or lactating.

Vaccine Components

BEC2 is purified from virus-free lipoprotein-free cell culture supernatants by Celltech, Ltd (Slough, England) using Protein A affinity chromatography and anion-exchange chromatography. The final product is >95% pure as determined by SDS-polyacrylamide gel electrophoresis. BEC2 is supplied in sterile phosphate buffered saline at concentration of 2.5 mg/ml in single-dose vials.

BCG (TheraCys™) is purchased from Connaught Laboratories (Swiftwater, Pa.) in vials containing $3.4 \times 10^8$ colony-forming units (CFU)/vial in a freeze-dried form. Immediately before administration, BCG is reconstituted with 3.4 ml of sterile diluent and then further diluted in normal saline if necessary. Vaccine is prepared by mixing 1 ml of BEC2 (2.5 mg) with 0.1 ml of the appropriate dilution of BCG immediately prior to administration.

QS21, supplied by Cambridge Bioscience, Inc. (Worcester, Mass.), is extracted from *Quillaja saponaria* Molina tree bark using silica and reverse-phase chromatography as previously described (Kensil, et al., 1991). It is supplied in 2.1 mg vials as a lyophilized powder and once reconstituted with sterile phosphate buffered saline, can be stored at 4° C. for not more than 14 days. Vaccine containing QS21 is prepared immediately prior to administration by mixing 1 ml of BEC2 (2.5 mg) with 100 μg of QS21. The dose of QS21 is selected based on a previous phase I clinical trial (Livingston, et al., 1994).

BEC2/BCG

The vaccine is injected intradermally into multiple rotated sites on weeks 0, 2, 4, 6, and 10; injections are given only into limbs in which the regional lymph node basin is intact. In patients who developed anti-GD3 antibodies, a sixth immunization is offered at a time when the anti-GD3 antibody titers returned to baseline.

The initial immunization contained 2.5 mg BEC2 mixed with $1 \times 10^7$ CFU of BCG. In the setting of grade III local toxicity, subsequent doses of BCG are attenuated 3-fold (i.e. $3 \times 10^6$ CFU, $1 \times 10^6$ CFU, $3 \times 10^5$ CFU, $1 \times 10^5$ CFU, $3 \times 10^4$ CFU, $1 \times 10^4$ CFU). Patients with a positive PPD (or a history of a positive PPD), are started at an attenuated BCG dose of $3 \times 10^6$ CFU.

BEC2/OS21

Vaccine is administered as a single subcutaneous injection using the identical schedule and dose of BEC2 as for the BEC2/BCG vaccine (weeks 0, 2, 4, 6, and 10). Each vaccine consisted of 2.5 mg BEC2 and 100 μg of QS21; the QS21 dose is not attenuated.

Serological Evaluation

Serum is collected pre-treatment, at the time of each immunization, and two weeks following each immunization and stored at −20° C. Serum is tested for the presence of BEC2 antibodies and anti-GD3 antibodies using an ELISA assay as previously described (Chapman, et al., 1994). Internal standards are run with each assay to ensure adequate and reproducible sensitivity. The specificity of the anti-BEC2 response is characterized by comparing the anti-BEC2 IgG response to the IgG response against MPC11, an isotype-matched mouse MAb (IgG2b) with framework sequences (Ng, et al., 1993). Ab3 antibodies are detected by their ability to bind BEC2 but not MPC11. The degree of binding of BEC2 versus MPC11 is compared by ELISA using a serum dilution that results in sub-maximal binding to BEC2 (absorbance values of approximately 0.5 are used). This is done firstly to ensure that the assay is carried out at a serum dilution corresponding to the linear portion of the titration curve for each serum sample and secondly, to standardize the assay allowing the data to be analyzed according to treatment group. The presence of Ab3 antibodies is confirmed in selected patients by exhaustively absorbing immune serum against agarose beads (Affigel 10, Bio-Rad Laboratories, Hercules, Calif.) coated with MPC11 until reactivity against MPC11 was not detected. The absorbed serum is then assayed for binding to BEC2.

A patient is considered to have developed anti-GD3 antibodies if at least two post-treatment sera samples reproducibly demonstrate a 4-fold or greater increase in anti-GD3 reactivity compared to the pre-treatment sample. This strict criterion was established based on our serological studies in patients immunized with BCG alone to avoid confusion with transient, low-level, non-specific reactivity that can be induced by BCG and other adjuvants. Attempts to characterize further the specificity of anti-GD3 responses employed mixed hemadsorption assays against $GD3^+$ allogeneic melanoma cell lines (Vadhan-Raj, et al., 1988) and immuno-thin layer chromatography (Chapman, et al., 1994).

Experimental Results:

Patient Characteristics

Fourteen patients are immunized with BEC2/BCG while 6 patients are immunized with BEC2/QS21. Patient characteristics are shown in Table 1. While the two groups of patients are relatively similar, the patients immunized with BEC2/BCG have a male predominance compared to the BEC2/QS21 group and are slightly older. Also, 21% of patients immunized with BEC2/BCG have either stage III with more than 4 lymph nodes positive or have stage IV disease while none of the BEC2/QS21 patients have these poor prognostic features.

TABLE 1

Characteristics of patients immunized with either BEC2/BCG or BEC2/QS21

| Patient characteristic | BEC2/BCG | BEC2/QS21 |
|---|---|---|
| N | 14 | 6 |
| Male:female | 9:5 | 3:3 |
| Median age (years) | 44.5 | 31.5 |
| Extremity primary site | 3 (21%) | 2 (33%) |
| Axial primary site | 10 (71%) | 4 (67%) |
| Unknown primary site | 1 (7%) | 0 |
| Stage II | 1 (7%) | 1 (16.5%) |
| Stage III | 12 (86%) | 5 (83.5%) |
| 1 lymph node | 6 (43%) | 2 (33%) |
| 2–4 lymph nodes | 4 (29%) | 3 (50%) |
| >4 lymph nodes | 2 (14%) | 0 |
| Stage IV | 1 (7%) | 0 |
| Median number of months from surgical excision to first immunization (range) | 2.7 (1–5.8) | 3.2 (0.93–4.7) |

Serological Responses

All patients in both trials develop IgG antibodies against BEC2 (Table 2). There is no meaningful difference between the median or range of anti-BEC2 IgG titers induced by BEC2/BCG and BEC2/QS21 (Table 2) nor in the number of immunizations required to induce anti-BEC2 IgG (data not shown). This suggests that both BCG and QS21 adjuvants are equally potent at augmenting anti-BEC2 antibody responses.

TABLE 2

Serological response rates in patients immunized with BEC2/BCG or BEC2 + QS21.

| VACCINE | ANTI-BEC2 ANTIBODIES | | ANTI-GD3 ANTIBODIES | |
|---|---|---|---|---|
| | % OF PATIENTS DEVELOPING ANTIBODIES | MEDIAN TITER (RANGE) | % OF PATIENTS DEVELOPING ANTIBODIES | TITERS |
| BEC2/BCG | 100 | 1:204800 (1:25600–1:1638,400) | 21 | 1:80, 1:160, 1:640 |
| BEC2/QS21 | 100 | 1:102400 (1:51200–1:204800) | 0 | |

In order to determine whether a portion of the anti-BEC2 response represents an Ab3 response, immune sera showing high titers of anti-BEC2 IgG is tested for binding MPC11, an isotype-matched mouse MAb (IgG2) in which 75% of the framework sequences are identical to the BEC2 framework sequences (unpublished). Preferential binding to BEC2, as demonstrated either by higher titer or higher absorbance readings, is observed in 11/14 (79%) patients immunized with BEC2/BCG and 5/6 (83%) of patients immunized with BEC2/QS21 implying that the majority of patients, immunization induces BEC2-specific IgG antibodies. Data from a representative patient (patient 13 immunized with BEC2/BCG) is shown in FIG. 1A.

In order to compare the relative specificity for BEC2 versus MPC11 for each treatment group, the absorbance readings for BEC2 binding are compared to the readings for MPC11 binding at a serum dilution that resulted in submaximal binding to BEC2 (absorbance at 405 nm approximately equal to 0.5). This standardizes the assay and ensures that the assay is carried out at a dilution corresponding to a linear portion of the titration curve for each serum sample. FIG. 1B shows the mean absorbance readings against BEC2 and MPC11 for patients immunized with BEC2/BCG or BEC2/QS21. In both treatment groups, the mean absorbance against MPC11 is lower than the reading against BEC2 and again implies that immunization induced BEC2-specific IgG. To confirm the presence of specific antibodies against BEC2 (i.e. Ab3), selected sera are exhaustively absorbed against MPC11 and then tested for binding to BEC2.

Figure 1A:
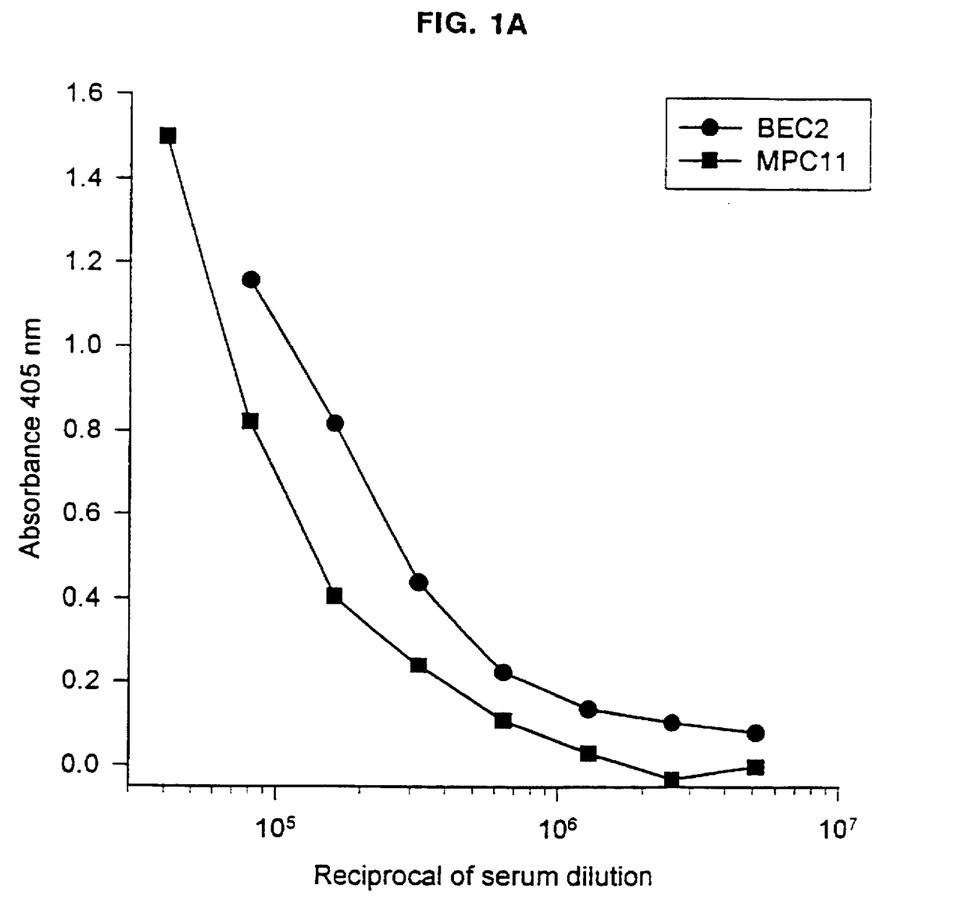
Figure 1B:
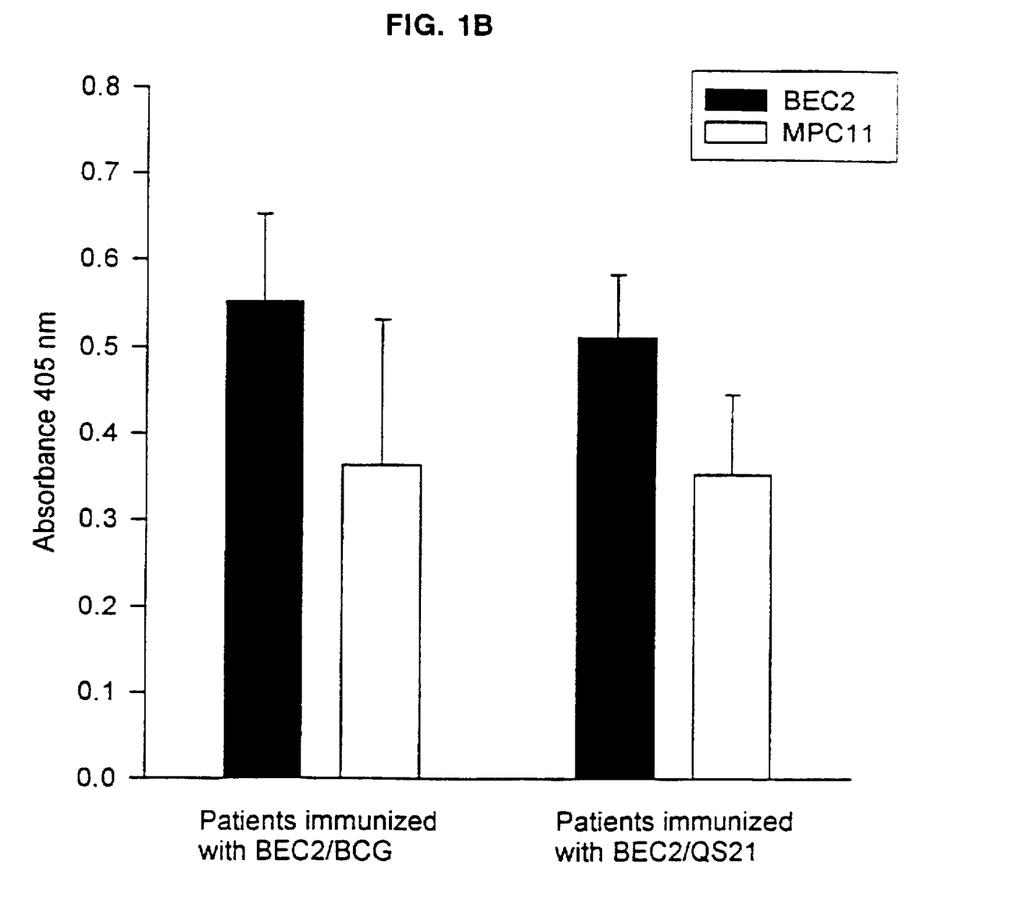
Figure 1C:
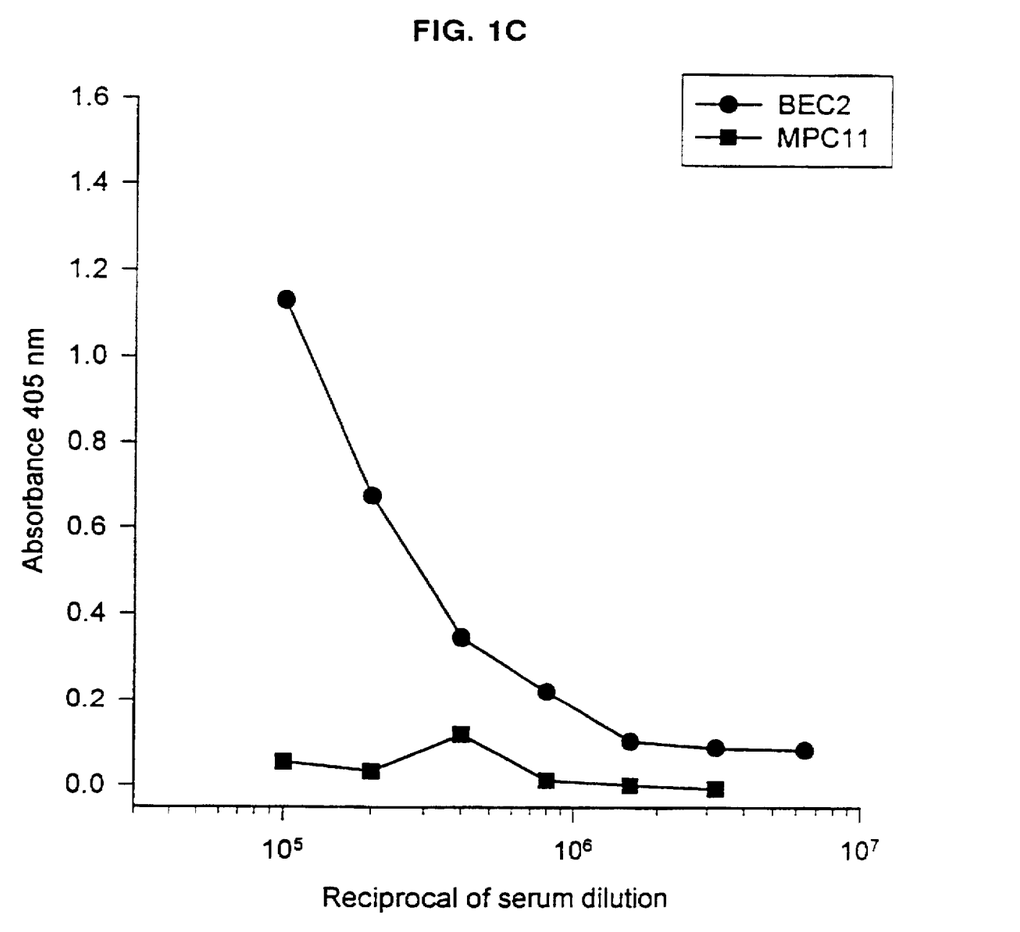

FIG. 1C shows the results of an experiment using the same serum specimen used in FIG. 1A. After absorption against MPC11, no anti-MPC11 reactivity remains but substantial reactivity against BEC2 is still observed demonstrating the presence of Ab3 antibodies.

Figure 2A:
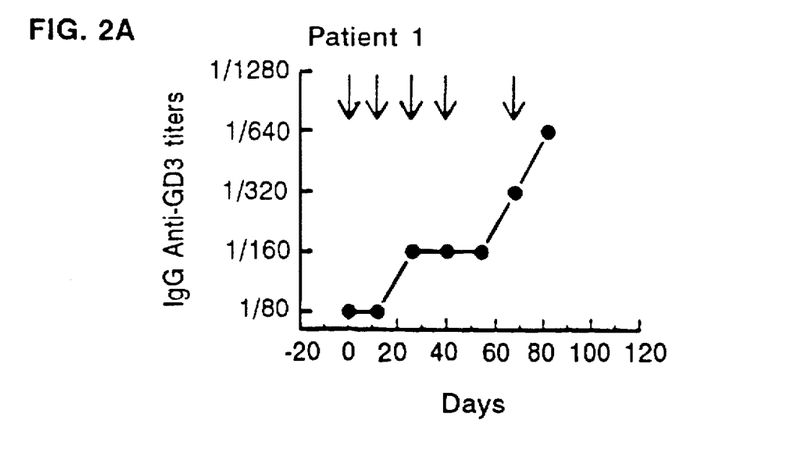
Figure 2B:
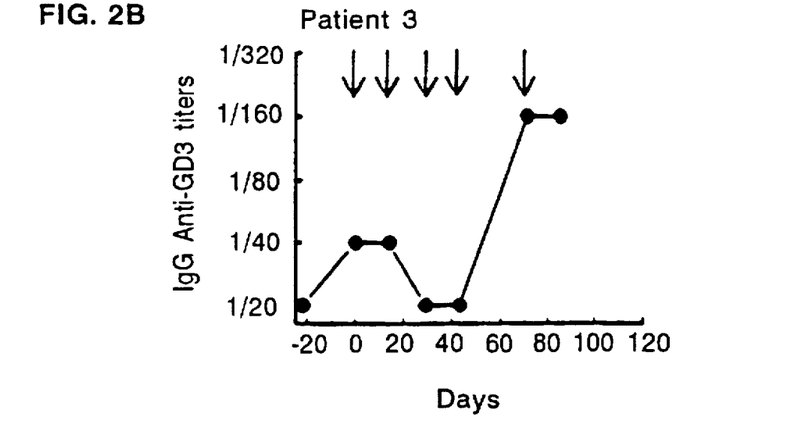
Figure 2C:
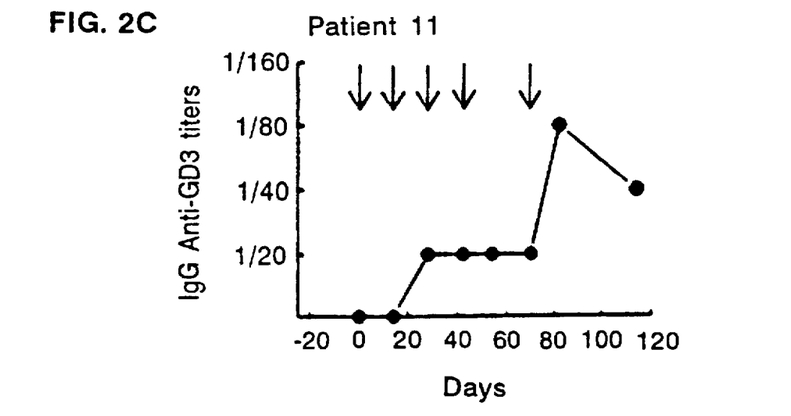

Anti-GD3 antibodies were detected by ELISA in 3/14 (21%) patients immunized with BEC2/BCG (Table 2) while no patient immunized with BEC2/QS21 developed detectable anti-GD3 antibodies. The anti-GD3 antibodies were detected with secondary antibodies against human IgG but not IgM suggesting they were of the IgG isotype. The titers of the anti-GD3 antibody responses are illustrated in FIG. 2 and ranged from 1:80 to 1:640.

Disease Recurrence and Overall Survival

Figure 3:
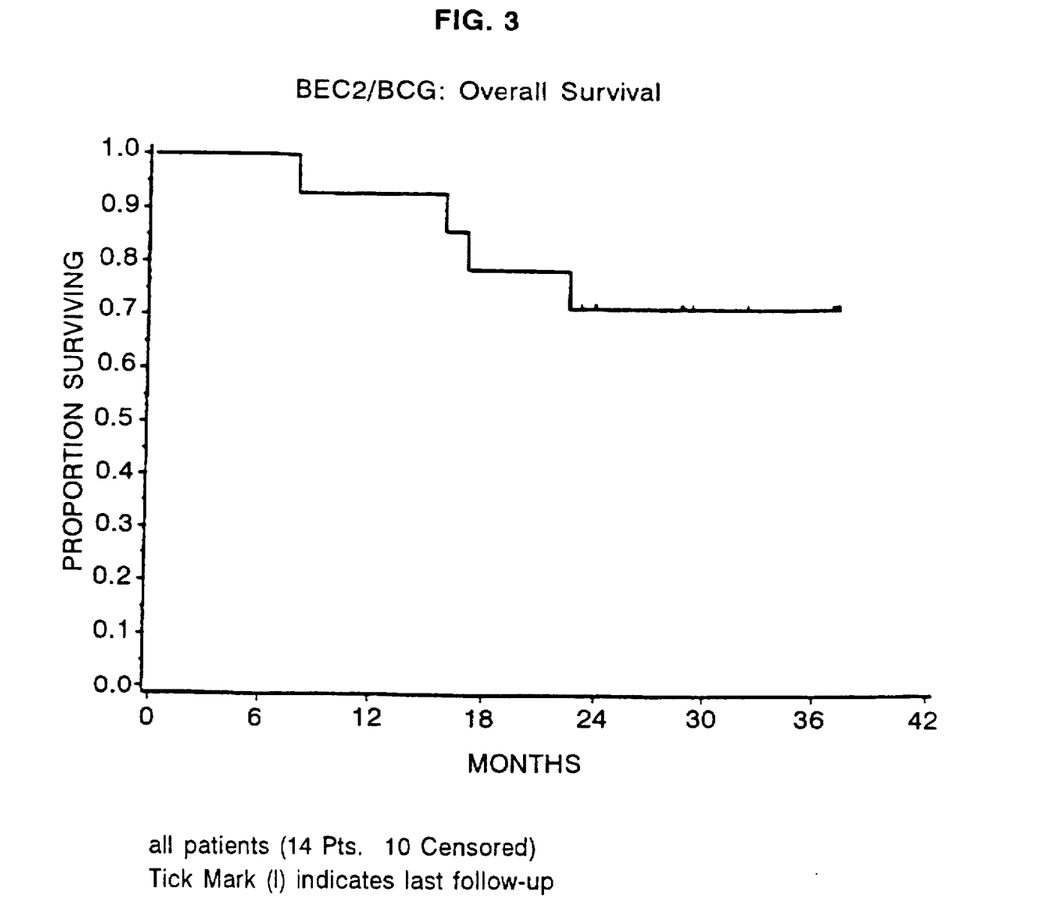
FIG. 3: Overall survival of patients immunized with BEC2/BCG (Kaplan-Meier Curve).

Surviving patients immunized with BEC2/BCG have been followed for a median of 2.4 years (2.2–2.9) and 10/14 patients (71%) remain alive. Of these 10 patients, 8 never recurred, 1 recurred with a solitary metastasis that has been resected, and 1 patient remains alive with metastatic disease. FIG. 3 shows that the overall survival rate plateaued suggesting that the disease-free status of the remaining patients may be durable. Two of the three patients who developed anti-GD3 antibodies, including one patient who had stage IV disease, remain free of disease.

The patients immunized with BEC2/QS21 have been followed for a median of 2 years and of the six patients immunized, 3 remain free of disease.

Toxicity

All patients immunized with BEC2/BCG experienced grade III toxicity at the sites of immunization characterized by inflammation, ulceration, and oozing. In one patient, the third immunization had to be delayed for 1 month to allow the previous vaccine sites to heal. All sites healed with minimal wound care and there were no instances of BCGosis. Eight patients experienced grade II fever, 3 noted grade II fatigue or malaise, and one patient had a transient grade II elevation in glucose. Grade I toxicities included elevated liver function tests (6 patients), hyperglycemia (3 patients), fatigue (3 patients), fever (1 patient), and hypocalcemia (1 patient).

All patients immunized with BEC2/QS21 also experienced inflammation at the sites of injection although only of grade II severity and of shorter duration; there was no ulceration or oozing. Two of the patients also noted grade II fever. Grade I toxicities included fatigue (4 patients), hyperglycemia (2 patients), neutropenia (2 patients), and diarrhea (1 patient).

Overall, immunizations are well-tolerated and no patient is removed from study because of adverse reactions.

HLA Class II Oligotyping

As an exogenous antigen, BEC2 may be taken up by antigen presenting cells, processed to peptides, and helper T cell epitopes presented by HLA class II molecules. In this way, BEC2 may provide T cell help for the B cell response against GD3. Therefore, applicants are interested in knowing the HLA class II type of the patients to determine whether there is any correlation between HLA class II type and immune response to BEC2 or overall survival.

TABLE 3

HLA class II genotyping of melanoma patients immunized with BEC2/BCG

| Pts | Oligotyping | | | | | | Serologically-defined alleles* | |
|---|---|---|---|---|---|---|---|---|
| # | DR alleles | | | | DQ alleles | | DR | DQ |
| 1 | B1*0701 | B1*1104 | B4*0101 | B3*02 | B1*0201 | B1*0301 | 7, 11 w53, w52 | 2, 7 |
| 3 | B1*0301 | B1*1103 | B3*0101 | B3*02 | B1*0201 | B1*0301 | 3, 11, w52 | 2, 7 |
| 4 | B1*07 | B1*0801 | B4*0101 | | B1*0201 | B1*0402 | 7, 8, w53 | 2, 4 |
| 5 | B1*0301 | B1*1103 | B3*0101 | B3*02 | B1*0201 | B1*0301 | 3, 11, w52 | 2, 7 |
| 6 | B1*1501 | B1*1104 | B5*0101 | B3*02 | B1*0602 | B1*0301 | 15, 11, w52 | 1, 7 |
| 7 | B1*1302 | B1*1306 | B3*02 | B3*0301 | B1*0603 | B1*0605 | 13, w52 | 1 |
| 8 | B1*1501 | B1*04 | B5*0101 | B4*0101 | B1*0602 | B1*0605 | 15, 4, w53 | 1 |
| 10 | B1*0301 | B1*0402 | B3*0101 | B4*0101 | B1*0201 | B1*0302 | 3, 4, w52, w53 | 2, 3 |
| 11 | B1*0102 | B1*1104 | B3*02 | B1*0501 | B1*0301 | | 1, 11, w52 | 7 |
| 12 | B1*14 | B1*04 | B3*02 | B4*0101 | B1*0503 | B1*0301 | 14, 4, w52, w53 | 1, 7 |
| 13 | B1*0701 | B1*1104 | B3*02 | B4*01 | B1*0201 | B1*0301 | 7, 11, w52, w53 | 2, 7 |
| 14 | B1*0301 | | B3*0101 | | B1*0201 | 3 | 2 | |

Class II oligotyping is performed in 12 of the 14 patients immunized with BEC2/BCG (Table 3); samples are not available in the remaining two BEC2/BCG patients. Oligotyping is not carried out in the BEC2/QS21 patients due to the small number of these patients. There is no apparent association between HLA class II genotype and induction of anti-GD3 antibodies, induction of anti-BEC2 antibodies, or survival.

HLA class II oligotyping is performed as described in Materials and Methods. DNA is extracted from PBMC except in patient #1 in whom DNA is extracted from hair bulbs. DNA is not available from patients 2 or 9. Serological designations are derived from the oligotyping data and are not directly determined.

The applicants compared the corresponding serologically-defined class II allele distribution among our patients with the distribution published for the Caucasian population in the United States in general (Rieger, et al). We used this reference group (N=232) since it best reflected the group of twelve melanoma patients. While there are no apparent differences at the DR locus, there is an apparent decrease in DQ1 frequency (43.7% vs. 25%) with a corresponding increase in the frequency of DQ2 (22.9% vs. 33.3%) and DQ7 (16.3% vs. 33.3%) among the melanoma patients. However, a formal statistical test is not performed due to the small sample size. These data are consistent with the hypothesis that certain HLA class II alleles, or the loss of certain alleles, may be associated with an increased risk of melanoma.

Discussion

These clinical trials extend our previous observations in melanoma patients immunized with BEC2 alone. In a previous study in which patients were immunized with BEC2 administered subcutaneously but without an immune adjuvant, only 55% of patients developed anti-BEC2 antibodies and only 1/20 developed detectable anti-GD3 antibodies (Chapman, et al., 1994). In the current studies in which patients are immunized with the same dose and schedule of BEC2 mixed with either BCG or QS21 adjuvant, all patients develop anti-BEC2 antibodies and at a significantly higher titer than seen in patients immunized without adjuvant. This difference is statistically significant (p=0.001, Fisher's exact test). In addition, 3/14 patients immunized with BEC2/BCG develop anti-GD3 antibodies while none of the 6 patients immunized with BEC2/QS21 develop anti-GD3 antibodies. Thus, both BCG and QS21 are potent adjuvants that enhance the anti-BEC2 antibody response but anti-GD3 responses are observed only in patients receiving BEC2/BCG.

This contrasts somewhat with what the applicants have observed previously with the MELIMMUNE anti-idiotypic MAb vaccine which mimics the high molecular weight-melanoma associated antigen (HMW-MAA). In that study, QS21 was superior to BCG in inducing anti-MELIMMUNE antibodies (Livingston, et al., 1995).

While antibody responses to carbohydrate antigens, such as GD3, are generally of the IgM isotype, it is interesting to note that the anti-GD3 responses detected after immunization with BEC2 are IgG. This is consistent with what we have observed previously in rabbits immunized with BEC2 (Chapman, et al., 1991) and may be due to the fact that as a protein that mimics GD3, BEC2 is potentially capable of providing T cell help necessary for isotype class switching.

An intriguing observation is that after a median follow-up of 2.4 years, 10/14 (71%) patients immunized with BEC2/BCG remain alive and 9/14 (64%) free of disease. This compares favorably with the survival of stage III melanoma patients in general (Livingston, et al., 1995) and stage III patients rendered free of disease after surgery (Balch, et al., 1992), and although the follow-up is relatively short, both previous observations (Livingston, et al., 1995) and the fact that no recurrences have been observed for the past 19 months suggest that most of the recurrences have already occurred. It is interesting to note that many long-term survivors did not have detectable serum antibodies against GD3 after BEC2 immunization. This may be due to inadequate sensitivity of the anti-GD3 serological assays;

alternatively, it may be that non-antibody mechanisms play a role in the protective effect observed. Randomized (Drepper, et al., 1993) and non-randomized trials (Parkinson, et al., 1992) using BCG alone in melanoma patients have not demonstrated an effect of BCG on disease-free survival, and so it is considered unlikely that BCG alone is responsible for the effect of BEC2/BCG on survival.

This disease-free survival rate in the BEC2/BCG patients contrasts with observations in patients from a previous study in which a similar population of patients were immunized with BEC2 without adjuvant (Broker, et al., 1986). In that study, none of the patients developed anti-GD3 antibodies and only 33% of patients were alive after a median follow-up of 2.8 years. These observations suggest that highly immunogenic formulations of BEC2 can induce anti-GD3 antibodies in patients and may contribute to prolonged survival.

The applicants determined the HLA class II type in the patients immunized with BEC2/BCG and found no apparent association between class II genotype and serological response to BEC2 or to disease-free survival. A previous report found that DQB1*0301 (corresponding serologically to DQ7), was more common among melanoma patients (56%) than among a healthy control group (27%) and that DQB1*0301 correlated with an increased risk of advanced disease (Chapman, et al., 1995). The applicants found a similar incidence of DQB1*0301 among our patients (58%) and also noted that the DQ7 allele frequency among our patients was higher than the frequency published for Caucasians in the U.S. The significance of these findings must be interpreted with caution given the small number of patients studied, and it remains unclear whether the incidence of DQB1*0301 (DQ7) differs significantly from a carefully matched control group. Despite this, it is of interest that the current study is now the second report of observations consistent with an increase in frequency of DQ7 among melanoma patients.

References of the Preceding Section:

1. Balch, C. M., Soong, S., Shaw, H. M., Urist, M. M. and McCarthy, W. H. An analysis of prognostic factors in 8500 patients with cutaneous melanoma. In: Balch, C. M., Houghton, A. N., Milton, G. W., Sober, A. J. and Soong, S. (eds.) Cutaneous Melanoma, Ed. 2nd. pp. 165-187. Philadelphia: J. B. Lippincott Company, 1992.
2. Brocker, E. B., Suter, L., Czarnetzki, B. M. and Macher, E. BCG immunotherapy in stage I melanoma patients. Does it influence prognosis determined by HLA-DR expression in high-risk primary tumors? Cancer Immunol Immunother, 23:155-157, 1986.
3. Caulfield, J., Barna, B., Murthy, S., Tubbs, R., Sergi, J., Mendendorp, S. and Bukowski, R. M. Phase Ia–Ib trial of an anti-GD3 monoclonal antibody in combination with interferon-α in patients with malignant melanoma. J Bio Response Mod, 9:319-328, 1990.
4. Chapman, P. B., Lonberg, M. and Houghton, A. N. Light chain variants of an IgG3 anti-GD3 monoclonal antibody and the relationship between avidity, effector functions, tumor targeting, and antitumor activity. Cancer Res. 50:1503-1509, 1990.
5. Chapman, P. B. and Houghton, A. N. Induction of IgG antibodies against GD3 in rabbits by an anti-idiotypic monoclonal antibody. J.Clin.Invest. 88:186-192, 1991.
6. Chapman, P. B., Livingston, P. O., Morrison, M. E., Williams, L. and Houghton, A. N. Immunization of melanoma patients with anti-idiotypic monoclonal antibody BEC2 which mimics GD3 ganglioside: Pilot trials using no immunological adjuvant. Vaccine Res. 3:59-69, 1994.
7. Chapman, P. B., McCaffery, M., Zuklys, K., Giorgio, N. and Houghton, A. N. Immunization with BEC2 anti-idiotypic monoclonal antibody that mimics GD3 ganglioside: Superiority of the intravenous route. Proc Am Assoc Cancer Res, 36:4931995. (Abstract)
8. Cheresh, D. A., Pierschbacher, M. D., Herzig, M. A. and Mujoo, K. Disialogangliosides GD2 and GD3 are involved in the attachment of human melanoma and neuroblastoma cells to extracellular matrix. J.Cell Biol. 102:688-696, 1986.
9. Creekmore, S., Urba, W., Koop, W., Ewel, C., Hecht, T., Smith, I., Janik, J., Steis, R., Fenton, R., Sharfman, W., Conlon, K., Sznol, M., Holmlund, J., Curti, B., Gause, B., Houck, M., Beveridge, J., Jones, M. and Longo, D. Phase IB/II trial of R24 antibody and interleukin-2 (IL2) in melanoma. Proc Am Soc Clin Oncol, 11:3451992. (Abstract)
10. Dippold, W. G., Knuth, A. and Meyer zum Buschenfelde, K. Inhibition of human melanoma cell growth in vitro by monoclonal anti-GD3-ganglioside antibody. Cancer Res. 44:806-810, 1984.
11. Drepper, H., Bieb, B., Hofherr, B., Hundeiker, M., Lippold, A., Otto, F., Padberg, G., Peters, A. and Wiebelt, H. The prognosis of patients with stage III melanoma. Prospective long-term study of 286 patients of the Fachklinik Horneide. Cancer, 71:1239-1246, 1993.
12. Hamilton, W. B., Helling, F., Lloyd, K. O. and Livingston, P. O. Ganglioside expression on human malignant melanoma assessed by quantitative immune thin-layer chromatography. Int.J.Cancer, 53:566-573, 1993.
13. HLA 1991. Proceedings of the Eleventh International Histocompatibility Workshop and Conference, pp. 1073-1074. Oxford: Oxford University Press, 1992.
14. Kabat, E., Wu, T., Reid-Miller, M., Perry, H. And Gottesmann, K. Sequences of Protein of Immunological Interest, U.S. Dept. Of Health and Human Services, U.S. Govt. Printing Office, 1987.
15. Kensil, C. R., Patel, U., Lennick, M. and Marciani, D. Separation and characterization of saponins with adjuvant activity from Quillaja saponaria Molina cortex. J.Immunol. 146:431-437, 1991.
16. Kensil, C. R., Barrett, C., Kushner, N., Beltz, G., Storey, J., Patel, V., Recchia, J., Aubert, A. and Marciani, D. Development of a genetically engineered vaccine against feline leukemia virus infection. J.Am. .Vet.Med.Assoc. 199:1423-1427, 1991.
17. Lee, J. E., Reveille, J. D., Ross, M. I. and Platsoucas, C. D. HLA-DQB1*0301 association with increased cutaneous melanoma risk. Int.J.Cancer. 59:510-513, 1994.
18. Livingston, P. O., Ritter, G., Oettgen, H. F. and Old, L. J. Immunization of melanoma patients with purified gangliosides. In: Oettgen, H. F. (ed.) Gangliosides and Cancer, pp. 293-300. New York: VCH Publishers, 1989.
19. Livingston, P. O., Adluri, S., Helling, F., Yao, T. J., Kensil, C. R., Newman, M. J. and Marciani, D. Phase 1 trial of immunological adjuvant QS-21 with a GM2 ganglioside-keyhole limpet haemocyanin conjugate vaccine in patients with malignant melanoma. Vaccine. 12:1275-1280, 1994.

20. Livingston, P. O., Wong, G. Y. C., Adluri, S., Tao, Y., Padavan, M., Parente, R., Hanlon, C., Jones Calves, M., Helling, F., Ritter, G., Oettgen, H. F. and Old, L. J. Improved survival in stage III melanoma patients with GM2 antibodies: A randomized trial of adjuvant vaccination with GM2 ganglioside. J.Clin.Oncol. 12:1036–1044, 1994.
21. Livingston, P. O., Adluri, S., Zhang, S., Chapman, P., Raychaudhuri, S. and Merrit, J. A. Impact of immunological adjuvants and administration route on HAMA response after immunization with murine monoclonal antibody MELIMMUNE-1 in melanoma patients. Vaccine Res. 4:87–94, 1995.
22. Mittelman, A., Chen, Z. J., Yang, H., Wong, G. Y. and Ferrone, S. Human high molecular weight melanoma-associated antigen (HMW-MAA) mimicry by mouse anti-idiotypic monoclonal antibody MK2-23: Induction of humoral anti-HMW-MAA immunity and prolongation of survival in patients with stage IV melanoma. Proc.Natl.Acad.Sci.,USA, 89:466–470, 1992.
23. Newman, M. J., Wu, J. Y., Coughlin, R. T., Murphy, C. I., Seals, J. R., Wyand, M. S. and Kensil, C. R. Immunogenicity and toxicity testing of an experimental HIV-1 vaccine in nonhuman primates. AIDS Res.Hum.Retroviruses, 8:1413–1418, 1992.
24. Ng, J., Hurley, C. K., Baxter-Lowe, L. A., Chopek, M., Coppo, P. A., Hegland, J., Kukuruga, D., Monos, D., Rosner, G., Schmeckpeper, B., Yang, S. Y., Dupont, B. and Hartzman, B. J. Large-scale oligonucleotide typing for HLA-DRB1/3/4 and HLA-DQB1 is highly accurate and reliable. Tissue.Antigens. 42:473–479, 1993.
25. Parkinson, D. R., Houghton, A. N., Hersey, P. and Borden, E. C. Biologic Therapy of Melanoma. In: Balch, C. M., Houghton, A. N., Milton, G. W., Sober, A. J. and Soong, S. (eds.) Cutaneous Melanoma, Ed. 2nd. pp. 522–541. Philadelphia: J. B. Lippincott Company, 1992.
26. Raymond, J., Kirkwood, J., Vlock, D., Rabkin, M., Day, R., Whiteside, T., Herberman, R., Mascari, R. and Simon, B. A phase Ib trial of murine monoclonal antibody R24 (anti-GD3) in metastatic melanoma. Proc.Am.Soc.Clin.Oncol. 10:2981991. (Abstract)
27. Rieger, R., Michaelis, A. and Green, M. M. *Glossary of Genetics, Classical and Molecular*, Ed.5th. Berlin: Springer-Verlag, 1991.
28. Tai, T., Cahan, L. D., Tsuchida, T., Saxton, R. E., Irie, R. F. and Morton, D. L. Immunogenicity of melanoma-associated gangliosides in cancer patients. Int.J.Cancer, 35:607–612, 1985.
29. Vadhan-Raj, S., Cordon-Cardo, C., Carswell, E. A., Mintzer, D., Dantis, L., Duteau, C., Templeton, M. A., Oettgen, H. F., Old, L. J. and Houghton, A. N. Phase I trial of a mouse monoclonal antibody against GD3 ganglioside in patients with melanoma: Induction of inflammatory responses at tumor sites. J.Clin.Oncol. 6:1636–1648, 1988.
30. White, A. C., Cloutier, P. and Coughlin, R. T. A purified saponin acts as an adjuvant for a T-independent antigen. Adv.Exp.Med.Biol. 303:207–210, 1991.
31. Wu, J. Y., Gardner, B. H., Murphy, C. I., Seals, J. R., Kensil, C. R., Recchia, J., Beltz, G. A., Newman, G. W. and Newman, M. J. Saponin adjuvant enhancement of antigen-specific immune responses to an experimental HIV-1 vaccine. J.Immunol. 148:1519–1525, 1992.

Second Series of Experiments:

Since the development of combination therapy over 20 years ago, no chemotherapeutic intervention has substantially prolonged the survival of small cell lung cancer (SCLC) patients from a median survival of 7–16 months.

Material and Methods:

Patients Selection

Patients who have a major response to initial therapy are injected intradermally on weeks 0,2,4,6 and 10 with 2.5 mg of BEC2 and $2 \times 10^7$ CFU of BCG. The dose of BCG is attenuated for skin toxicity superior or equal to 3. Patients characteristics are a median age of 63 years old, a median KPS of 80%, an elevated LDH2 in two out six patients and hyponatremia in two out six patients. (Table 4)

Of 8 SCLC patients, 6 patients are evaluable for response with a median follow up of 36 months (range 16–43 months). (table 4)

Vaccine Components

BEC2 is purified from virus-free lipoprotein-free cell culture supernatants by Celltech, Ltd (Slough, England) using Protein A affinity chromatography and anion-exchange chromatography. The final product is >95% pure as determined by SDS-polyacrylamide gel electrophoresis. BEC2 is supplied in sterile phosphate buffered saline at concentration of 2.5 mg/ml in single-dose vials.

BCG (TheraCys™) is purchased from Connaught Laboratories (Swiftwater, Pa.) in vials containing $3.4 \times 10^8$ colony-forming units (CFU)/vial in a freeze-dried form. Immediately before administration, BCG is reconstituted with 3.4 ml of sterile diluent and then further diluted in normal saline if necessary. Vaccine is prepared by mixing 1 ml of BEC2 (2.5 mg) with 0.1 ml of the appropriate dilution of BCG immediately prior to administration.

TABLE 4

Immunization of small cell lung cancer patients with BEC2 and BCG

| | Date of Dx | Complete Rx | Date BEC2 | Last FU | | |
|---|---|---|---|---|---|---|
| MB | 9/28/92 | 3/24/93 | 8/24/93 | 12/1/95 | | |
| JE | 4/7/92 | 9/17/92 | 2/12/93 | 12/15/95 | | |
| JF | 10/26/92 | 3/23/93 | 6/1/93 | 11/6/95 | | |
| MM | 10/9/92 | 3/15/93 | 6/11/93 | 2/18/94 | | |
| ES | 7/2/92 | 1/5/93 | 2/5/93 | 3/24/94 | | |
| RS | 11/13/92 | 4/19/93 | 7/23/93 | 10/3/95 | | |
| | Survival from D | Survival from BEC2 | LDH | Na | Stage | Gender |
| MB | 38.63 | 27.63 | 153 | 135 | LD | F |
| JE | 44.90 | 34.53 | 164 | 141 | LD | M |
| JF | 36.87 | 29.60 | 226 | 126 | ED | F |
| MM | 16.57 | 8.40 | 368 | 139 | ED | F |
| ES | 21.00 | 13.73 | 196 | 139 | ED | F |
| RS | 35.13 | 26.73 | 165 | 138 | LD | M |

BEC2/BCG

The vaccine is injected intradermally into multiple rotated sites on weeks 0, 2, 4, 6, and 10.

The initial immunization contained 2.5 mg BEC2 mixed with $1 \times 10^7$ CFU of BCG. In the setting of grade III local toxicity, subsequent doses of BCG are attenuated 3-fold (i.e. $3 \times 10^6$ CFU, $1 \times 10^6$ CFU, $3 \times 10^5$ CFU, $1 \times 10^5$ CFU, $3 \times 10^4$ CFU, $1 \times 10^4$ CFU). Patients with a positive PPD (or a history of a positive PPD), are started at an attenuated BCG dose of $3 \times 10^6$ CFU.

Experimental Results:

Disease Recurrence and Overall Survival of SCLC Patients

All SCLC patients immunized with BEC2/BCG developed anti-BEC2 and ⅙ developed anti-GD3 antibodies. The median survival was not reached but will exceed 36 months.

Figure 4:
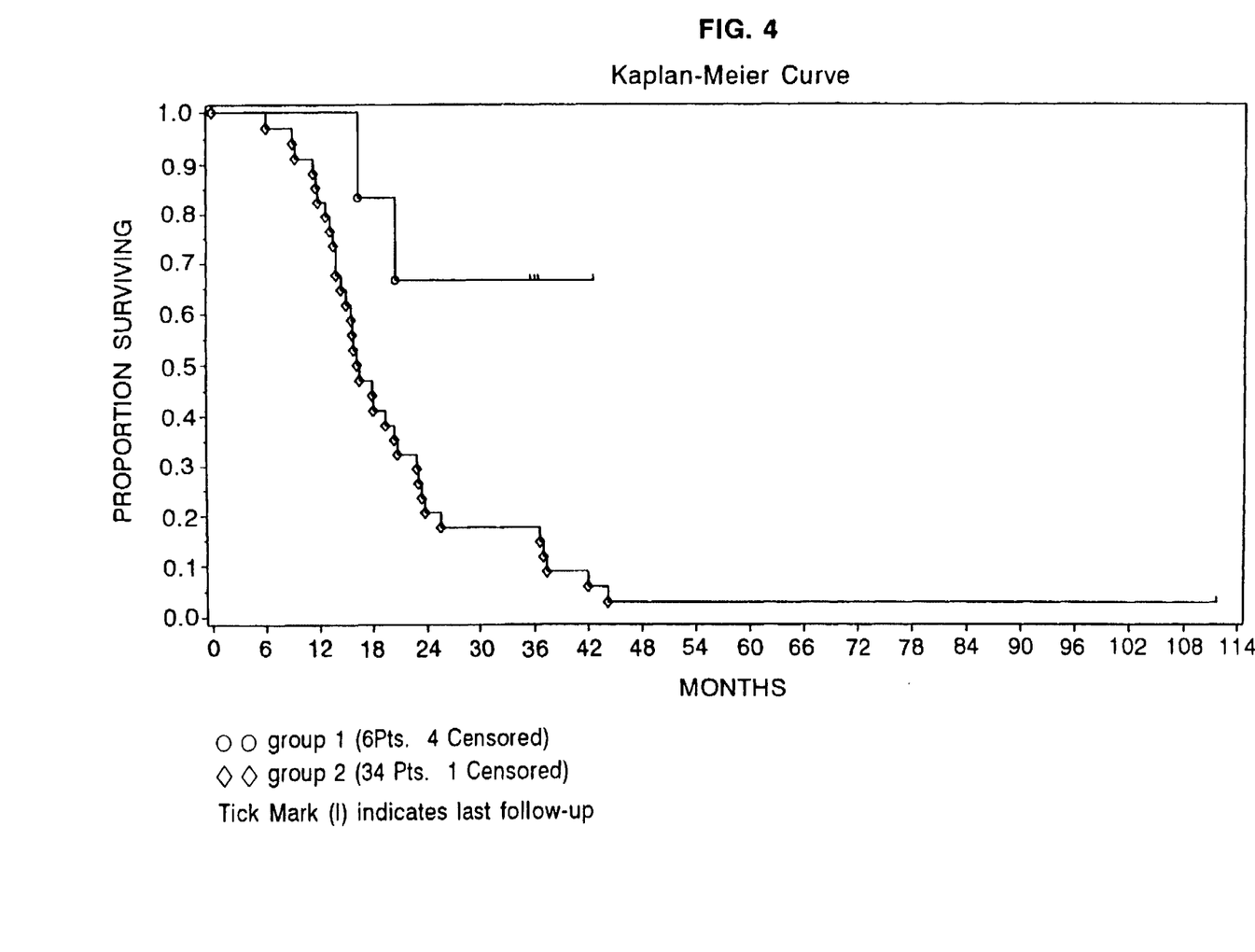
FIG. 4: Overall survival of SCLC patients immunized with BEC2/BCG (Kaplan-Meier Curve).

For survival comparison, 34 patients who had major tumor responses after at least 6 cycles of chemotherapy –/+ radiation served as reference group. There were no differences in prognostic characteristics between the reference group and patients given BEC2/BCG. Median survival of the reference group and patients given BEC2/BCG is 16.2 months (95% Cl; 14–21 months). Using a log-rank test, a significant difference in Kaplan-Meier survival curves was demonstrated (p=0.019). At 36 months the survival rate was 18% (95% Cl; 8–35%) for the reference group versus 67% (95% Cl; 26–92%) for patients receiving BEC2/BCG (FIG. 4). Patients immunized with BEC2/BCG showed a long median and excellent 36 months survival.

What is claimed is:

1. A composition for stimulating and enhancing in a subject to which the composition is administered, production of antibodies which recognize GD3 ganglioside, comprising an effective amount of anti-idiotypic monoclonal antibody, designated BEC2, produced by the hybridoma designated ATCC Accession No. HB 10153, an effective amount of BCG and a pharmaceutically acceptable vehicle.

2. A composition of claim 1, wherein the effective amount of BEC2, produced by the hybridoma designated ATCC Accession No. HB 10153, ranges from about 0.5 mg to 25 mg.

3. A method for stimulating and enhancing in a subject production of antibodies which recognize GD3 ganglioside comprising administering an effective amount of the composition of claim 1.

4. A method for treating melanoma in a subject comprising administering to the subject an effective amount of the composition of claim 1.

5. A method for increasing the survival rate of small cell lung cancer patients comprising administering to small cell lung cancer patients an effective amount of the composition of claim 1.

6. A method of claim 5, wherein the patients are treated with a chemotherapeutic agent.

7. A method of claims 3, 4, or 5, wherein an effective amount of the composition is administered into at least one site on definite time intervals.

8. A method of claims 3, 4, or 5, wherein attenuated doses of BCG are administered.

9. A method of claim 8, wherein an effective amount of the composition is administered in one or more sites.

* * * * *

UNITED STATES PATENT AND TRADEMARK OFFICE
CERTIFICATE OF CORRECTION

PATENT NO. : 5,792,455
DATED : AUGUST 11, 1998
INVENTOR(S) : CHAPMAN ET AL.

It is certified that error appears in the above-identified patent and that said Letters Patent is hereby corrected as shown below:

Col. 16, lines 22-24, claim 1: please delete the phrase "stimulating and enhancing in a subject to which the composition is administered, production of antibodies which recognize GD3 ganglioside," and please add the phrase after the words "A composition for", treating cancer associated with expression of GD3 ganglioside, Col. 16, lines 5-6, claim 3: please delete the phrase "stimulating and enhancing in a subject to which the composition is administered, production of antibodies which recognize GD3 ganglioside," and please add the phrase after the words "A composition for", treating cancer associated with expression of GD3 ganglioside, .

UNITED STATES PATENT AND TRADEMARK OFFICE
CERTIFICATE OF CORRECTION

PATENT NO. : 5,792,455
DATED : August 11, 1998
INVENTOR(S) : Chapman et al.

It is certified that error appears in the above-identified patent and that said Letters Patent is hereby corrected as shown below:

Col. 16, please add allowed claim 10: <u>The composition of claim 1, wherein the cancer is melanoma.</u>

Col. 16, please add allowed claim 11: <u>The composition of claim 1, wherein the cancer is small cell lung carcinoma.</u>

Signed and Sealed this

Fifteenth Day of June, 1999

Attest:

Q. TODD DICKINSON

*Attesting Officer*     *Acting Commissioner of Patents and Trademarks*